United States Patent [19]
Wiley et al.

[11] 3,944,495
[45] Mar. 16, 1976

[54] METAL DIALKYLDITHIOPHOSPHATES

[75] Inventors: Morris A. Wiley; Raymond C. Schlicht, both of Fishkill; James O. Waldbillig, Wappingers Falls, all of N.Y.

[73] Assignee: Texaco Inc., New York, N.Y.

[22] Filed: Feb. 19, 1974

[21] Appl. No.: 443,567

[52] U.S. Cl. ............... 252/75; 252/327 E; 260/399; 260/429.9; 260/948; 260/950; 260/952
[51] Int. Cl.² ..................... C09K 3/00; C10M 1/48
[58] Field of Search ................. 252/75, 76, 32.7 E; 260/948, 950, 952, 399, 429.9

[56] References Cited
UNITED STATES PATENTS

| | | | |
|---|---|---|---|
| 2,631,132 | 3/1953 | McDermott | 260/952 X |
| 2,905,683 | 9/1959 | Goldsmith | 260/950 |
| 3,029,268 | 4/1962 | Goldsmith | 260/948 |
| 3,640,872 | 2/1972 | Wiley et al | 252/75 |

*Primary Examiner*—Harris A. Pitlick
*Attorney, Agent, or Firm*—T. H. Whaley; C. G. Ries; Robert A. Kulason

[57] ABSTRACT

Novel metal dialkyldithiophosphates prepared from oxalkylated long, straight-chain alcohols, acids and mercaptans and their incorporation in lubricating oils to enhance the lubricity and other properties thereof; and a method for operation of an automatic transmission incorporating said oils.

8 Claims, No Drawings

METAL DIALKYLDITHIOPHOSPHATES

BACKGROUND OF INVENTION

There exists a constant demand for improved performance of lubricating oil compositions. Nowhere does this appear to be more true than in the formulation of automatic transmission fluids, torque fluids and the like. One such demand and concern, illustratively, is the development of novel lubricity compositions incorporating significant friction reducing properties in addition to the anit-corrosion and anti-oxidant characteristics normally known to inhere, for example, in the usual short and branched chain dialkyl, dialkylphenoxy, and dialkylphenoxyalkyl dithiophosphates in present use, which, indeed, while they may be innocuous in reducing friction are known often to actually impart a profrictional effect to the lubricant compositions in which they are incorporated.

An automatic transmission is a complex hydraulic mechanism which incorporates the functions of a torque converter, wet clutches and planetary gearing in a relatively sealed unit. As the wet clutch plates engage and their relative velocities decrease to 0, a substantial reduction in the coefficient of friction is necessary to obtain a smooth lock-up of the clutch plates.

If compositions could be secured incorporating, illustratively, the anti-corrosion and anti-wear properties of the foregoing conventional phosphates minimizing, or eliminating, the use of these compounds in automatic transmission fluids and the like, but contributing simultaneously and economically to the requisite reduction in the coefficient of friction of the clutch face surfaces, the result would represent a significant advance in the state of the art.

SUMMARY OF INVENTION

It is accordingly a primary object of this invention to provide novel compounds which constitute improved lubricant additives incorporating a complex of desirable properties for inclusion in lubricating oils and most notably a lubricity in automatic transmission fluids and torque fluids such as will effect a reduction of friction in the transmission shifting operation.

Other objects and advantages of this invention will become evident from the following description.

According, it has now been discovered that novel metal dialkyldithiophosphates prepared from oxyalkylated long, straight-chain alcohols, acids and mercaptans provide additives for lubricating oils, and particularly automatic transmission fluids and torque fluids, which when incorporated therein, are characterized by desirable anti-oxidant, anti-corrosion and anti-wear properties but most significantly, by improved extreme pressure properties, reduced torque fluids deposits and unexpectedly enhanced lubricity characteristics.

DETAILED DESCRIPTION OF THE INVENTION

The lubricant additives of this invention are characterized by the novel metal dialkyldithiophosphates of the general formula:

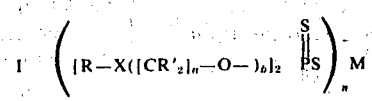

wherein:

R is a straight chain saturated aliphatic radical containing about 4 to 30 or more carbon atoms, and preferably from 10 to 20 carbon atoms;

X is an oxygen, sulfur, carbonyloxy, sulfone, sulfate, amino, or alkyl substituted amino radical, and said alkyl moiety contains from about 1 to about 6 carbon atoms;

R' is a hydrogen, alkyl or aryl radical or mixtures thereof; each of said alkyl and aryl containing respectively about 1 to 6 and 6 to 9 carbon atoms, the term "aryl" including for purpose of this discussion alkylaryl and arylalkyl radicals.

$a$ is an integer of from about 2 to about 12 and preferably about 2 to about 4;

$b$ is an integer of from about 1 to about 10;

$n$ is an integer corresponding to the valence of M; and is preferably the integer 2; and M is an alkali metal, an alkaline earth metal or a transition metal, illustratively sodium, potassium magnesium calcium, copper, cadmium, silver, and most desirably zinc.

Particularly preferred of the zinc-containing phosphates coming within the foregoing structural formula are those wherein R is a straight chain saturated aliphatic radical containing about 6 to 18 carbons, X is oxygen, sulfur, or a carbonyloxy group; R' is hydrogen; $a$ is the integer 2; $b$ is an integer from about 2 to about 10; and $n$ is as a consequence of the divalent character of zinc, the integer 2.

Further illustrative of the dithiophosphate additives employed in the practice of the invention are: zinc bis[di(octadecyloxyethoxyethyl)dithiophosphate] of the formula:

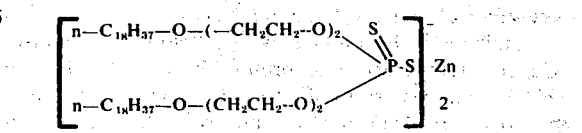

zinc bis[di(n-octadecyloxynonalethoxyethyl)dithiophosphate] of the formula:

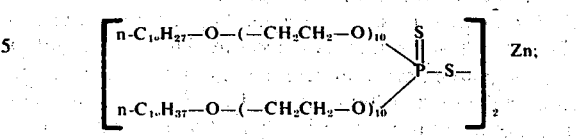

and zinc bis[di(hexadecylmercatoethyl)dithiophosphate] of the formula:

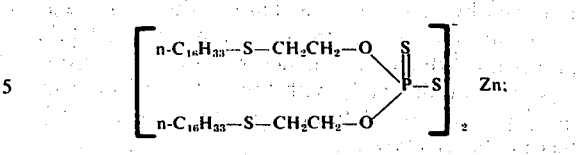

and zinc bis[di(stearoyloxytetraethoxyethyl)dithiophosphate] of the formula:

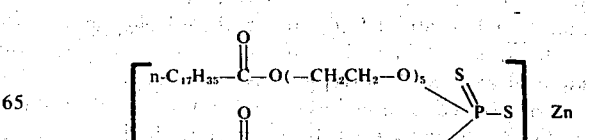

The metal dialkyldithiophosphates of the invention are novel compounds prepared by reaction of an oxyalkylated alcohol, mercaptan, carboxylic acid, or other "active hydrogen" compound with phosphorus pentasulfide to form the corresponding oxyalkylated phosphoric acid which is then neutralized by reaction with a basic metal salt.

By way of illustration, an active hydrogen source such as, for example, alcohols, carboxylic, sulfinic and sulfonic acids, amines and the like reacted with cyclic ethers, carbonates, sulfites, sulfates, ketals, and acetals of dihydric alcohols with or without the use of catalysts, such as bases, acids, Friedel-Crafts catalysts and the like, may be used to supply the oxalkylated, e.g. oxyethylated, oxypropylated or oxybutylated intermediate. Specific illustrations of the foregoing ethers, carbonates and the like are ethylene oxide, propylene oxide, butylene oxide, propylene carbonate, butylene carbonate, ethylene carbonate, oxetane and alkyl-oxetanes, such as 2,2-dialkyl oxetane, furans, and 1,3-alkane carbonates. By way of further illustration, the active hydrogen compound, such as lauryl alcohol which is then reacted with the phosphorus pentasulfide ($P_2S_5$) to yield a substituted dialkyldithiophosphoric acid which is readily neutralized with a metallic base to provide a metal salt which may function as the desired additive or, optionally, be metathetically reacted with the salt of another metal to effect an exchange of the metallic constituents.

The foregoing sequence comprises therefore the steps of reacting an adduct alcohol of the formula:

wherein each of R, X, R', and b has the meaning recited hereinabove in Formula I, with phosphorus pentasulfide at a temperature of preferably about 160° F. to 180° F. in a mole ratio of about 2:1 respectively and in the presence of an inert organic solvent such as benzene; and contacting the resulting reaction mixture wherein is contained the dialkyldithiophosphoric acid resulting from reaction of said alcohol and phosphorus pentasulfide with a base metal salt in a mole ratio of said acid to said salt corresponding approximately to the valence of the metal of said salt. The latter reaction occurs conveniently at room temperature and in the same solvent in which the acid reactant was formed. The metal salt is most desirably first formed into a paste using water in an amount ranging desirably from about 0.75 to about 1.50 moles of water per mole of metal salt consumed in the reaction. The water is thereafter removed by azeotropic distillation with sequential isolation and recovery of the desired metal dialkyldithiophosphate, which may, as described above, be further reacted metathetically with the salt of another metal coming within the definition of "M" in Formula I appearing hereinabove.

In accordance with the invention, the foregoing dialkyldithiophosphates are included in an automatic transmission fluid or torque fluid comprising at least 80 weight percent of a mineral lubricating oil and from about 0.01 to about 5.0 percent of said phosphate.

The fluid oil in which the foregoing additives are incorporated while having, as a result of the practice herein defined, and as indicated above, very desirable lubricity and consequently, efficacious hydrodynamic frictional effect and extreme pressure properties as well as desirable anti-oxidation, anti-wear and anti-corrosion properties, will generally be a fully formulated fluid, and particularly a fully formulated automatic transmission fluid containing various amounts of conventional additives as well.

Such fluid is generally characterized by an SUS viscosity at 210° F. of 49 to 60, a viscosity index of at least 150 and a pour point below −40° F. and meets the essential Dexron specifications set by General Motors Corporation for automatic transmission fluids.

A suitable automatic transmission fluid for use in the practice of the invention contains typically and by way of further illustration, from about 0.5 to about 8.0 wt. % of an oil concentrate of a polymer of mixed alkyl esters of methacrylic acid having from about 25,000 to about 1,250,000 molecular weight and preferably from about 100,000 to about 500,000.

The foregoing alkyl methacrylate esters are, desirably, mixtures of these esters wherein the alkyl substituents contain from about 4 to 18 carbon atoms. A commercially available methacrylate ester of this type which is used primarily to impart the desired viscosity, adjust and improve the viscosity index and pour point of lubrication oils is one in which the alkyl substituent is a mixture of lauryl, butyl, stearyl, and hexyl groups.

A dispersant is generally incorporated in the lubricant formulation, as well. An effective dispersant comprises a composition resulting from mixture of a substituted succinic compound, selected from succinic type acids and anhydrides of the formulae:

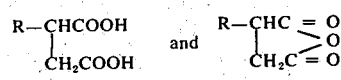

wherein R is a large substantially aliphatic hydrocarbon radical, having from about 50 to 200 carbon atoms, with at least one half of a molar equivalent amount of a polyethylene polyamine and, in the case of the acid, heating the resulting mixture to effect acylation and remove the water formed thereby. The anhydride may react, however, without external heating and hence may be heated only if further reaction of the intermediate amic acid is desired. Suitable amines are diethylene triamine, triethylene tetramine, tetraethylene pentamine and amino-alkylated heterocyclic compounds. The reaction involves amidation of a dicarboxylic acid or anhydride thereof with a polymer to produce aminosubstituted acyclic diamides, amic acids, polymeric amides, or a combination of these types of products. It will be noted that the amide groups may further react to form imide groups in the process.

The term "equivalent" in the paragraph preceding means that a minimum of one-half mole of alkenylsuccinic anhydride or acid per mole of amine is required. This is the least amount of acid which will react with all of the amine added (via amic acid or acyclic polyamide formation). The maximum amount of acid or anhydride possible to react is one-half mole per primary or secondary amino group. Generally, one or two moles of acid or anhydride per mole of amine, regardless of the total number of nitrogen atoms, is preferred. The reaction product is effective in amounts ranging from about 0.25 to 5.0 wt. %. Methods for preparing the polyethylene polyamide reaction products are well known and have been described in U.S. Pat. No. 3,131,150 and 3,172,892.

An amine anti-oxidant may be used in this fully formulated transmission fluid. Effective anti-oxidants are the aryl-substituted amine anti-oxidants exemplified by the phenyl naphthyl amines, phenylene diamine, phenothiazone and diphenylamine. A particularly preferred anti-oxidant is phenyl alpha naphthylamine. The anti-oxidants are effective in a concentration ranging from about 0.1 to 2.5 wt. %.

A metal, and preferably, a zinc di(alkylphenoxypolyalkoxyalkyl) dithiophosphate may also be included. This compound is represented by the formula:

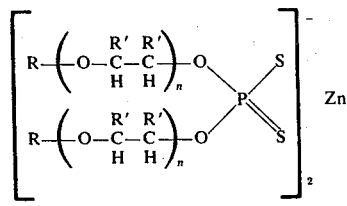

in which R represents phenyl substituted with a branched aliphatic radical having from 6 to 15 carbon atoms. R' is hydrogen or an alkyl radical having from 1 to 4 carbon atoms and $n$ is an integer from 1 to 10. Particularly effective compounds in this class are the zinc di(nonylphenoxyethyl) dithiophosphate, zinc di(dodecylphenoxyethyl) dithiophosphate is prepared by reacting a nonylphenolethylene oxide adduct with phosphorus pentasulfide followed by neutralization of the acid formed with a basic zinc compound, such as zinc carbonate, zinc oxide or zinc hydroxide. The general preparation of the compounds in this class is disclosed in U.S. Pat. No. 2,344,395 and 3,293,181. In use, it is convenient to prepare a mineral oil solution of the zinc di($C_{6-15}$alkylphenoxy-polyalkoxyalkyl) dithiophosphate containing from 50 to 75 wt. % of the zinc salt. The salts are effective oxidation and corrosion inhibitors for automatic transmission fluids when employed in a concentration ranging from about 0.1 to 5.0 wt. % based on the hydraulic fluid.

Anti-foam agents are conventionally employed in hydraulic fluids because the fluids are rapidly circulated in operation and air can be entrapped. For this purpose, a silicone fluid of high viscosity, such as a dimethyl silicone polymer having a kinematic viscosity at 25° C. of about 1000 centistokes and above is prefarably employed. A very satisfactory anti-foam agent for this purpose is prepared by diluting 10 grams of a dimethyl silicone polymer (1000 centistrokes at 25° C.) with kerosene to provide a solution of 100 cubic centimeters. From 0.005 to 0.025 percent by weight of this concentrate is generally employed in the hydraulic fluid A fully formulated lubricating oil composition for automatic transmission service can be prepared from a parafinic base oil having an SUS at 100° F. of about 100. A desirable base oil blend may be formulated, in addition, comprising 65% of a furfural-refined, acid-treated, clay-contacted, solvent-dewaxed, paraffin base distillate having an SUS at 100° F. of 100; a viscosity index about 100, a flash above 385° F. and a pour below +10° F., 22% of an acid-treated naphthenic base distillate having an SUS at 100° F. of 60, a flash above 300° F. and a pour below −40° F.; and 13% of a paraffin base residuum which has been propane-deasphalted, solvent-dewaxed and clay-contacted and which has an SUS viscosity at 210° F. of 160, a flash of about 540° F. and a pour below 5° F. This base oil mixture had a flash above 375° F., a pour below 0° F. and a viscosity index of about 93.

A fully formulated automatic transmission fluid for use herein may comprise a base oil blend such as the foregoing and may contain from about 0.5 to 8 wt. % of an oil concentrate containing about 35% by weight of a basic amino nitrogen-containing addition type copolymer of mixed alkyl esters of methacrylic acid, that is, copolymers comprising butyl, lauryl, stearyl and di-methyl amino-ethyl methacrylates in approximately 21:53:22:4 weight ratios (as described in U.S. Pat. No. 2,737,496); about 0.25 to 5.0 wt. % of an oil concentrate containing about 33% of the reaction product of approximately 1:1 mole ratio of tetraethylene pentamine and alkenyl succinic anhydride in which the alkenyl radical is polybutene of approximately 1200 average molecular weight (U.S. Pat. No. 3,172,892); about 0.1 to 2.5 wt. % of phenyl alpha naphthylamine, about 0.1 to 5 wt. % of an oil concentrate containing about 50% of zinc di(nonylphenoxyethyl) dithiophosphate and from about 0.01 to 5 wt. % of a dithiophosphate of the invention. It is to be noted the nonyl group in the zinc di(nonylphenoxyethyl) dithiophosphate is highly branched.

The present invention is further illustrated by the following examples:

EXAMPLE I

This example illustrates the preparation of the metal dialkyldithiophosphate of oxyalkylated long straight-chain alcohols, mercaptans and acids used in the practice of the invention.

a. Zinc bis[di(n-octadecyloxyethoxyethyl)dithiophosphate] was prepared as follows: 358 grams (1 mole) of n-octadecyloxyethoxyethyl alcohol was reacted with 56 grams (0.25 mole) of phosphorus pentasulfide in 500 ml of benzene solvent. The reaction took place at 160° F. for a period of two hours. The product, di(n-octadecyloxyethoxyethyl) dithiophosphoric acid was then neutralized with 22 grams (0.27 mole) of zinc oxide. The zinc oxide was made into a paste with water before addition of the foregoing acid. The water charged to the zinc oxide totalled 20 ml. The neutralization reaction with the formation of the product salt was permitted to proceed for about 30 minutes with stirring at room temperature, and azeotroped to dryness by refluxing thereafter at a maximum of 180° F. The resulting zinc bis[di(n-octadecyloxyethoxyethyl) dithiophosphate] was stripped at 200° F. at a reduced pressure of less tha 1 millimeter mercury (mm Hg.). The yield of zinc salt was 416 grams and was characterized by the following analysis:

| % zinc: | 4.0; calculated: 3.88 |
|---|---|
| % phosphorus: | found 3.5; calculated: 3.68 |
| % sulfur: | found 6.7; calculated: 7.6 | b. Zinc bis[di(n-octadecyloxynonaethoxyethyl)dithiophosphate] was prepared in the manner described in Example Ia except that 710 grams of n-octadecyloxynonaethoxyethyl alcohol was necessary to provide 1 mole equivalent of alcohol reactant.

The zinc oxide was refluxed with the dithiophosphoric acid provided by the previous step at 192° F. as a maximum temperature after reaction for one half hour at room temperature, and after cooling and filtering of the reaction product, was stripped at a temperature up to 180° F. and at a reduced pressure of 0.125 mm Hg. The yield of product was 740 grams and showed the following analysis:

| % zinc: | found: 2.0; calculated: 2.11 |
| % phosphorus: | found: 2.4; calculated: 2.01 | c. Zinc bis[di(n-hexadecylmercaptoethyl) dithiophosphate] was prepared by the process of Example Ia hereof substituting, however, 151 grams (0.5 mole of reactant n-hexadecyl mercapto ethanol for the alcohol of Example Ia and 28 grams of 0.125 mole of phosphorus pentasulfide. The zinc oxide was reacted in an amount of 11 grams of 0.125 mole thereof with the acid formed by the phosphorus pentasulfide and alcohol but was first formed into a paste with 11 ml of water. The latter reaction proceeded as in Example Ia but the reflux temperature did not exceed 175° F. The product was stripped from the reaction mixture after cooling and filtering at a temperature of up to 180° F. and about 2 mm mercury (Hg) pressure. The yield of product was 177 grams and was characterized further as follows:

| % zinc: | found: 3.7; calcualted: 4.5 |
| % sulfur: | found: 16.3; calculated: 17.6 | d. Zinc bis[di(stearoyloxytetraethoxyethyl) dithiophosphate] was prepared according to the procedure of Example Ia substituting 498 grams (equivalent to 1.0 mole) of stearyloxytetraethoxyethyl alcohol therein. This alcohol was azeotroped to dryness before being added to the $P_2S_5$. The zinc oxide was employed in an amount of 18 grams (0.275 mole) which was admixed with 15 ml of water. The reflux temperature was not permitted to exceed 170° F. and stripping of the product was undertaken at a maximum of 180° F. and 0.275 mm Hg. pressure. The yield of product was 525 grams characterized as follows:

| % zinc: | found: 2.6; calculated: 2.92 |
| % phosphorus: | found: 2.6; calculated: 2.76 |
| % sulfur: | found: 4.6; calculated: 5.7 |

EXAMPLE II

This example illustrates the valuable properties of the additives of the invention when incorporated in a standard paraffin base oil.

The zinc bis[di(n-octadecyldiethoxy) dithiophosphate] of Example Ia (referred to in Table I appearing hereinafter as Compound "A"); the zinc bis[di(n-stearyltetraethoxyethyl) dithiophosphate] of Example Id (referred to in Table I as Compound "D"); and the zinc bis[di(n-hexadecylmercaptoethyl) dithiophosphate] of Example Ic (referred to in Table I as Compound "C"); were each mixed in the proportions recited in Table I with a paraffinic base oil having an SUS at 100° F. of about 95 to about 105. The resulting composition containing Compound D also contained 2.5% polyisobutylene (~1200 m.w.) succinamic acid derivative of tetraethylene pentamine as dispersant.

The foregoing base oil with the zinc dialkyldithiophosphates of the oxyethylated compounds indicated were tested for their frictional effects, torque fluid deposit, transmission fluid screening, wear resistance and anticorrosion activity with a control sample of the foregoing lubricant oil from which the additive compositions of the invention were absent. This control sample is referred to in Table I as the "Control".

The frictional effects were determined in a Low Velocity Friction Test designated "LVT" in Table I. This test was conducted using a General Motors type of frictional surface, that is a test plate identical in composition to Borg Warner's SD-715 clutch plates, in sliding contact with steel. The coefficients of friction were determined at decreasing speeds, i.e. from about 40 feet per minute (ft/min.) down to 1 ft/min. The test temperature was 250° F. and the applied load was 120 pounds per square inch (psi).

The foregoing lubricant oil formulations were also subject to the standard Torque Fluid Deposit Test, MacCoull Corrosion Test, 4-Ball Wear Test and Mean Hertz Load Test Procedure.

The Torque Fluid Deposit Test, designated "TFD" in Table I, was undertaken in each instance at 350° F. for 24 hours and the 100° F. viscosity increases determined. The deposit formed is measure in milligrams.

The MacCoull Corrosion Test, described in U.S. Pat. No. 2,709,682 and designated as "MacCoull" in Table I, proceeded at 350° F. for a period of 10 hours.

The effectiveness of the oils tested is determined in this procedure by bearing weight loss (BWL) measured in milligrams and neutralization number (NN) over the duration of the test.

The 4-Ball Wear Test, designated as the "4-Ball Wear" in Table I, is also a well-known laboratory test procedure used for determination of the anti-wear properties of a lubricant oil. The test machine employed comprises a system of four steel balls, three of which are in contact with each other in one plane in a fixed triangular position in a reservoir containing the oil sample, and a fourth ball above and in contact with the other three. In carrying out the test, the upper ball is rotated while it is pressed against the lower three at any desired pressure by means of a suitable weight applied to a lever arm, and the diameters of the scars on the three lower balls are measured by means of a low power microscope. The average diameter, in millimeters, measured in two directions on each of the three lower balls, is taken as a measure of the antiwear characteristics of the lubricant. The results given in Table I were conducted at 200° F. for a period of 2 hours, employing new ½ inch diameter first grade steel SKF balls at a speed of 600 revolutions per minute and under a 40 kilogram load.

The results of the Mean Hertz Load Test, also a measure of wear, appear under the designation "Hertz" in Table I. This well-known laboratory procedure is described in U.S. Pat. No. 2,600,058.

All of the test compounds manifested significant anti-frictional properties as indicated by the decrease of friction with decreasing sliding speeds in the Low Viscosity Friction Tests (LVT) of Table I even at the reduced levels at which they were incorporated in the base oil. The stearyl oxyethylated phosphate, Compound D of Table I showed, in addition, a significant increment in extreme pressure activity over the base oil, the "Control" of Table I. All of the additives of the invention appearing in Table I reduced substantially the deposit forming tendencies of the base oil as shown in the Torque Fluid Deposit Test (TFD). The additives of Table I also evidenced the anti-wear effects typical of other and conventional metal dialkyldithiophosphates.

TABLE I

| Compound | Blended (% P by weight) | Dispersant | LVF Friction Coefficient 40 ft/min | LVF Friction Coefficient 1.0 | T.F.D. Dep. mg. | T.F.D. % Vis. Inc. | MacCoull BWL(mg) | MacCoull NN | 4-Ball Wear | Hertz |
|---|---|---|---|---|---|---|---|---|---|---|
| A | .0125 | — | .080 | .032 | 1208 | very high | — | — | .432 | 22 |
| D | .0125 | 2.5 | .133 | .111 | 8 | 69 | 142 | 5.0 | .445 | 19 |
| C | .0125 | — | .148 | .116 | 852 | 46.6 | 49 | 1.2 | — | 18 |
| C | .025 | — | .115 | .062 | 546 | 80 | 19 | 1.0 | .669 | 17 |
| Control | — | — | .130 | .204 | 2585 | 588 | 136 | 11.6 | .932 | 17 |

The foregoing additives of the invention, derived from the ethoxylated alcohols, have, in addition, demonstrated their utility as friction reducing agents in simulated high energy-input transmission testing.

It will be evident that the terms and expressions which have been employed are used in terms of desription and not of limitation. There is no intention in the use of such terms and expressions of excluding equivalents of the features shown and described or portions thereof and it is recognized that various modifications are possible within the scope of the invention claimed.

We claim:

1. An automatic transmission fluid comprising at least about 80 wt. % of a mineral lubricating oil and from about 0.01 to 5.0 wt. % of an alkyl dithiophosphate represented by the formula:

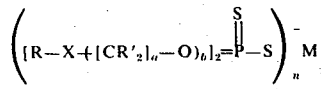

wherein:
R is a straight-chain aliphatic radial containing from about 4 to 30 carbon atoms;
X is carbonyloxy;
R' is selected from a hyrogen, alkyl, and aryl radical;
M is selected from an alkali metal, an alkaline earth metal, and a transition metal;
$a$ is an integer of from about 2 to about 12;
$b$ is an integer of from about 1 to about 10; and
$n$ is an integer corresponding to the valence of M.

2. A composition according to claim 1 wherein M is zinc.

3. A composition according to claim 1 wherein R is a straight-chain alkyl radical of from 10 to 20 carbon atoms.

4. A composition according to claim 1 wherein R' is hydrogen and $a$ is the integer 2 and $b$ is an integer of from about 1 to 10.

5. A composition according to claim 1 wherein said dithiophosphate is zinc bis[di)n-stearayloxytetraethoxyethyl) dithiophosphate].

6. A composition according to claim 1 wherein said automatic transmission fluid includes about 0.5 to 10 wt. % of a polymer of mixed alkyl esters of methacrylic acid having a molecular weight of from 25,000 to 1,250,000; about 0.25 to about 5.0 wt. % of a dispersant resulting from the reaction of a polyalkylene polyamine and a compound selected from an alkenyl succinic acid and an alkenyl succinic anhydride, about 0.1 to about 2.5 wt. % of an amine antioxidant and about 0.1 to 5 wt. % of a metal dialkyl phenoxyalkyl dithiophosphate.

7. A composite according to claim 6 wherein said automatic transmission fluid includes a base oil comprised of about 65% furfural refined, acid-treated, clay-contacted, solvent-dewaxed paraffin base distillate; about 22% of an acid-treated naphthenic base distillate; and about 13% of a paraffin base residuum which has been prepared, deasphalted, solvent-dewaxed and clay-contacted, and having a flash above 375° F., a pour below 0° F. and a viscosity index of about 93.

8. A method for operating an automatic transmission which comprises supplying to and running said transmission on a fluid oil composition comprising at least about 80% of a mineral lubricating oil and from about 0.01 to 5.0 wt. % of an alkyl dithiophosphate represented by the formula:

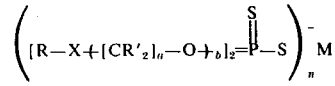

wherein:
R is a straight-chain aliphatic radical containing from about 4 to 30 carbon atoms;
X is carbonyloxy;
R' is selected from a hydrogen, alkyl and aryl radical;
M is selected from an alkali metal, an alkaline earth metal, and a transition metal;
$a$ is an integer of from about 2 to about 12;
$b$ is an integer of from about 1 to about 10;
$n$ is an integer corresponding to the valence of M.

* * * * *